US00PP19684P2

(12) United States Plant Patent
Lamb et al.

(10) Patent No.: US PP19,684 P2
(45) Date of Patent: Feb. 10, 2009

(54) ***ANTHURIUM* PLANT NAMED 'TWYANBD18'**

(50) Latin Name: *Anthurium hybrida*
Varietal Denomination: TWYANBD18

(76) Inventors: Ann E. Lamb, Sebring, FL (US); Marianne E. Knauss, Longwood, FL (US)

( * ) Notice: Subject to any disclaimer, the term of this patent is extended or adjusted under 35 U.S.C. 154(b) by 0 days.

(21) Appl. No.: 11/906,501

(22) Filed: Oct. 2, 2007

(51) Int. Cl.
*A01H 5/00* (2006.01)

(52) U.S. Cl. ..... Plt./369

(58) Field of Classification Search ..... Plt./369, Plt./365

See application file for complete search history.

*Primary Examiner*—Annette H Para
*Assistant Examiner*—S. B. McCormick Ewoldt

(57) ABSTRACT

A new *Anthurium* plant particularly distinguished by having medium-sized, triangular, bright-red, very shiny spathes, upright, branched, dense, leafy growth habit and contrasting, firm/leathery, very shiny, dark metallic leaves that become dark-green with maturity, is disclosed.

1 Drawing Sheet

Genus and species: *Anthurium hybrida.*
Variety denomination: 'TWYANBD18'.

BACKGROUND OF THE NEW PLANT

The present invention comprises a new and distinct cultivar of *Anthurium,* botanically known as *Anthurium hybrida,* and hereinafter referred to by the cultivar name 'TWYANBD18'. The new cultivar originated from a hybridization made in 2003 in Apopka, Fla., USA. The female parent was the *Anthurium* plant 'Pink Paradise' (U.S. Plant Pat. No. 11,657), while the male parent was the proprietary *Anthurium* plant 'H-43' (unpatented).

The new cultivar was selected in March 2005 from the results of the hybridization and has been asexually reproduced repeatedly by tissue culture in Apopka, Fla., USA over a two and one-half year period. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1) Medium sized, triangular, bright red, very shiny spathes;
2) Upright, branched, dense, leafy, growth habit; and
3) Contrasting, firm/leathery, very shiny, dark metallic leaves which become dark-green with maturity.

DESCRIPTION OF PHOTOGRAPH

This new *Anthurium* plant is illustrated by the accompanying photograph which shows the overall plant habit including blooms, buds and foliage of the plant. The colors shown are as true as can be reasonably obtained by conventional photographic procedures. The photograph is of a 23-month old plant grown in a greenhouse in Apopka, Fla.

DESCRIPTION OF THE NEW CULTIVAR

The following detailed description sets forth the distinctive characteristics of 'TWYANBD18'. The data which define these characteristics were collected from asexual reproductions carried out in Apopka, Fla. The plant history was taken on 23-month old plants which were planted from tissue culture in 25-cm pots and grown in a greenhouse with average daily temperatures of 85° F.–95° F. and average nightly temperatures of 72° F. to 78° F. Observations were made in March 2007. Color readings were taken under natural light in the greenhouse. Color references are primarily to the R.H.S. Colour Chart of The Royal Horticultural Society of London (R.H.S.) (2001).

DETAILED BOTANICAL DESCRIPTION

Classification:
- *Family.*—Aracea.
- *Botanical.*—*Anthurium hybrida.*
- *Common.*—*Anthurium.*

Parentage:
- *Female parent.*—*Anthurium* plant 'Pink Paradise' (U.S. Plant Pat. No. 11,657) with pink spathes.
- *Male parent.*—'H-43', a proprietary *Anthurium* plant with shiny, very dark-red spathes (unpatented).

Growth:
- *Form.*—Upright, symmetrical, with outward pointing leaves; plant wider than tall.
- *Growth and branching habit.*—Upright stems, dense, branched habit (basal, axillary branching), with many leaves and flowers; vigorous growth habit, plant produces numerous branches, leaves and flowers.
- *Height* (*measured from soil to top of canopy*).—48 cm to 52 cm.
- *Height* (*measured from soil to top of inflorescences*).—57 cm to 61 cm (flowers at, among and above the top of the foliage).
- *Width* (*area of spread*).—69 cm to 76 cm.

*Time to produce a finished flowering plant.*—Single micro cutting to liner: 14 to 16 weeks. 10 cm pot from liner: 7 to 8 months (first flowers). 15 cm pot from liner: 10 to 12 months. 20 cm pot from liner: 14 months.

*Growth rate.*—Typical of commercial *Anthurium* cultivars.

*Root description.*—Thick fleshy roots with finer laterals; between RHS N170D and RHS 196D; RHS 179B where exposed to light; RHS 151D root tips.

*Durability of foliage to stresses.*—Durable, holds up well under typical commercial practice.

*High temperature tolerance.*—To about 104° F. without damage.

*Low temperature tolerance.*—To about 55° F. without damage.

Stems:

*Number of stems per plant.*—16.

*Length (from soil line to the junction of the last two unrolled leaves).*—12 cm.

*Diameter (measured from about 6 cm above the soil surface).*—1.4 cm.

*Internode length.*—1.4 cm.

*Color.*—Immature: Between RHS 145B to RHS 145C sheathed with colors between RHS 147D to RHS 146D (green) cataphylls faintly tinged with between RHS 180C to RHS 180D. Mature: RHS 146D sheathed with dried cataphylls RHS 200B in RHS 199B (brown).

*Appearance (shape).*—Upright, cylindrical, round, thick with regularly spaced petioles and short internodes; cataphylls are present and nonpersistant; surface appearance is smooth and glossy.

*Pubescence.*—Absent.

*Aspect.*—Upright.

*Strength.*—Sturdy, tough, upright.

*Cataphylls.*—Shape and arrangement: Lanceolate, mucronate, acute, one or two keeled; base of cataphyll clasps the stem. Length: 5.5 cm to 12.0 cm. Width: 3.2 cm (flattened). Texture: Inside: Shiny, smooth. Outside: Glossy. Color: Between RHS 147D to RHS 146D faintly tinged with colors between RHS 180C to RHS 180D, becoming RHS 200B and RHS N199B with senescence.

Leaves:

*Arrangement and type.*—Alternate, simple, single leaf per petiole; midrib on lower surface is keeled.

*Quantity of leaves per stem.*—6 per main stem; fewer leaves on younger axillary branches.

*Length.*—18 cm to 28 cm.

*Width (natural).*—12 cm to 16 cm.

*Width (flattened).*—15 cm to 18 cm.

*Shape.*—Ovate.

*Apex.*—Acuminate, mucronate.

*Base.*—Cordate.

*Margin.*—Entire, with some broad undulations; leaf blade flat or somewhat folded upward lengthwise.

*Appearance (on both surfaces).*—Smooth, medium thickness, rigid, firm/leathery, very shiny/metallic sheen, dulling with age.

*Pubescence (on both surfaces).*—Absent.

*Immature leaf color.*—Upper surface: Between RHS N186A to RHS 187A tinged with RHS 200A. Lower surface: RHS 200B tinged with RHS 148A.

*Mature leaf color.*—Upper surface: Darker and greener than, but closest to RHS 147A. Lower surface: Between RHS 146A to RHS 147A.

*Venation.*—Pinnate. Venation color: Upper surface: Immature: Same as surrounding tissue. Immature midrib: RHS N186C tinged with RHS 148A (green). Mature: RHS 146B. Mature midrib: Between RHS 146A to RHS 147B. Lower surface: Immature: Between RHS N186C to RHS 186D. Immature midrib: Between RHS N186C to RHS 187C. Mature: Between RHS 147B to RHS 146B. Mature midrib: Between RHS 147B to RHS 146B.

*Petiole.*—Aspect: Vertical and upright when newly emerged, becoming about 35° to 45° from the vertical axis with maturity. Length (from base of leaf to junction of petiole and stem): 29 cm to 36 cm. Diameter: Distal (measured in the center below the geniculum and above the petiole wing tip): 0.45 cm. Proximal: 0.11 cm. Color: Immature: Between RHS 183A to RHS 185A tinged with RHS 148A. Mature: Between RHS 146B to RHS 147B.

*Geniculum.*—Length: 2.5 cm to 4.2 cm. Diameter: 0.45 cm to 0.50 cm. Aspect: Straight or curved upward. Color: Immature: Between RHS 183A to RHS 185A tinged with RHS 148A. Mature: Between RHS 146B to RHS 147B.

*Wing.*—Length: 3.9 cm (tip of wing acute or flush with petiole). Diameter: 0.5 cm. Color: Between RHS 147C to RHS 146C tinged with RHS 183C.

Inflorescence:

*Arrangement.*—Spathe/spadix atop peduncle, emerges from petiole sheath; peduncle attached to stem at leaf axil; inflorescences mostly clustered along the center of the plant; self-cleaning.

*Aspect.*—Upright straight, vertical when newly emerged, leaning somewhat outward with age.

*Height.*—57 cm to 61 cm.

*Depth.*—2.5 cm (spathe folded upward lengthwise).

*Flowering habit and season.*—Continuous flowering year round, but most prolific in winter and spring.

*Number of inflorescences per plant.*—13 inflorescences and buds.

*Buds.*—Shape is lanceolate, length is 7.5 cm to 9.3 cm, width is 0.8 cm to 1.1 cm and color is between RHS 46B to RHS 45A while the proximal end is tinged with RHS 46A.

*Fragrance.*—Absent.

*Rate of inflorescence opening.*—About every 14 days, 2 to 3 new inflorescences emerge.

*Longevity on plant.*—4 to 5 weeks.

*Longevity as cut flower.*—3 weeks.

Spathe:

*Appearance.*—Medium sized, triangular, bright-red, very shiny; margins fold upward lengthwise, apex often curves downward; very shiny when new, becoming glossy with age, medium thickness, firm/leathery, slightly concave between veins.

*Arrangement/aspect.*—Variable; typically horizontal and often curved downward distally.

*Pubescence (on both surfaces).*—Absent.

*Shape.*—Broad ovate with a truncate to slightly cordate base.

*Margin.*—Entire, with some broad undulations.

*Apex.*—Acute to acuminate, mucronate.

*Base.*—Slightly cordate.

*Longevity.*—4 to 5 weeks with good color.

*Size.*—Length: 7.5 cm to 11.5 cm. Width (natural): 5.0 cm to 7.5 cm. Width (flattened): 6.0 cm to 8.5 cm.

*Color.*—When opening: Front side: Very shiny RHS 47A tinged with RHS 147B around base of spadix.

Rear side: Between RHS 47B to RHS 47C, apex tinged with RHS 145A (green). Fully opened: Front side: Between RHS 50A to RHS 50B; around base of spadix RHS 50B. Rear side: Between RHS 50B to RHS 50C. Fading to: Between RHS 50A to RHS 50B; RHS 48A around base of spadix, often variably tinged with RHS 146A.

Spadix:

*Appearance.*—Columnar, upright, affixed atop very short stipe at junction of peduncle and spathe.

*Arrangement/aspect.*—Upright, near vertical, or tilted outward.

*Shape.*—Columnar, narrower, tapered at tip.

*Margin.*—Round in transverse section.

*Apex.*—Bluntly rounded, obtuse.

*Base.*—Bluntly rounded.

*Size.*—Length: 4.2 cm to 4.7 cm. Diameter: 0.7 cm.

*Color (immature).*—Proximal: Between RHS 51A to RHS 51B. Distal: Between RHS 41B to RHS 41C.

*Color (mature).*—RHS 185D.

Flowers:

*Arrangement.*—Flowers reduced, tightly packed on spadix.

*Type.*—Bisexual, reduced, minuscule; female flowers receptive first, followed by male flowers.

*Shape.*—Individual flowers roughly pyramidal in shape, tightly packed on the spadix; flowers sessile on spadix; face of individual flower flat and square or diamond shaped; pistil in center, protruding, surrounded by anthers; four triangular tepals at corners.

*Diameter.*—0.20 cm.

*Height.*—0.20 cm from base to tip of pistil; stigma protrudes about 0.10 cm when receptive.

*Number of female flowers per spadix.*—175.

*Number of male anthers per flower.*—About 8 (minuscule; not clearly visible).

Peduncle:

*Length.*—45 cm.

*Diameter.*—0.40 cm.

*Angle.*—Straight, upright or curved outward.

*Strength.*—Sturdy, somewhat flexible.

*Color.*—Immature: Between RHS 183A to RHS 185A tinged with RHS 148A. Mature: Between RHS 146B to RHS 147B.

Reproductive organs:

*Anther color.*—Same as surrounding spadix tissue.

*Pollen amount.*—Sparse.

*Pollen color.*—RHS 155D (white).

*Stigma color.*—RHS 62D.

*Ovary color.*—RHS 62D.

Fruit and seed set: Seed production has not been observed to date.

Disease and insect resistance: No particular resistance or susceptibility different from other *Anthurium* varieties.

COMPARISON WITH PARENTAL AND COMMERCIAL CULTIVARS

'TWYANBD18' differs from the female parent *Anthurium* plant 'Pink Paradise' (U.S. Plant Pat. No. 11,657), by having shiny, bright-red spathes, while 'Pink Paradise' has very large, cordate pink spathes and lobes flushed with green. 'TWYANBD18' has immature leaves that are very dark with a metallic sheen and become dark-green with maturity, while 'Pink Paradise' has leaves that are uniformly green. In addition, 'TWYANBD18' has an upright, highly branched growth habit with outward pointing leaves, while 'Pink Paradise' has an upright, symmetrical, clumping, growth habit that is less dense with fewer basal branches.

'TWYANBD18' differs from the male parent *Anthurium* plant 'H-43' (unpatented) by having shiny, bright-red spathes, while 'H-43' has shiny, very dark-red spathes. 'TWYANBD18' has an upright, highly branched growth habit with outward pointing leaves, while, 'H-43' has an upright, rounded growth habit that is less dense with fewer basal branches and larger leaves. In addition, 'TWYANBD18' has inflorescences that lean somewhat outward with age, while 'H-43' has inflorescences that lean more outward with age. 'TWYANBD18' is also more tolerant of adverse conditions, while 'H-43' has spathes and foliage that tend to fade if the plant is exposed to high temperatures.

'TWYANBD18' differs from the commercial variety 'Pippi' (U.S. Plant Pat. No. 14,475), by having larger spathes, folded upward lengthwise, while 'Pippi' has smaller, flatter spathes. 'TWYANBD18' has spathes that are shiny, bright-red and tinged with green at the base, while 'Pippi' has spathes that are uniformly red and not as shiny. In addition, 'TWYANBD18' has immature leaves that are very dark with a metallic sheen and become dark-green with maturity, while 'Pippi' has immature leaves that are green with darker veins.

'TWYANBD18' differs from the co-pending *anthurium* 'TWYANBD9' (U.S. application Ser. No. 11/906,885) in that 'TWYANBD18' has smaller spathes (length is 7.5 cm to 11.5 cm and width is 5.0 cm to 7.5 cm) than 'TWYANBD9' (length is 12.0 cm to 20.0 cm and width is 8.0 cm to 10.0 cm). Additionally, 'TWYANBD18' has smaller peduncles (45.0 cm) than 'TWYANBD9' (45.0 cm to 58.0 cm).

I claim:

1. A new and distinct cultivar of *anthurium* plant as shown and described herein.

* * * * *

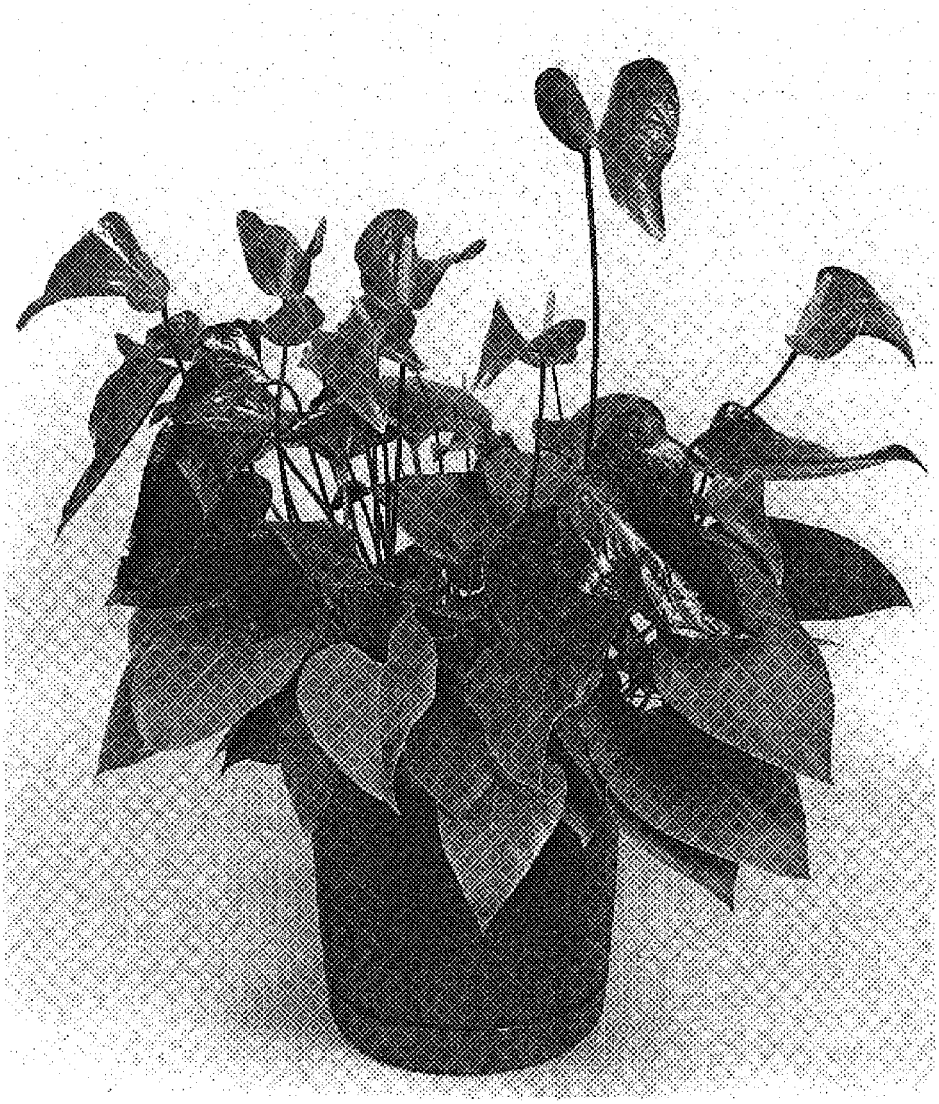

UNITED STATES PATENT AND TRADEMARK OFFICE

CERTIFICATE OF CORRECTION

PATENT NO. : PP 19,684 P2
APPLICATION NO. : 11/906501
DATED : February 10, 2009
INVENTOR(S) : Ann E. Lamb It is certified that error appears in the above-identified patent and that said Letters Patent is hereby corrected as shown below:

Title page, item [73] should read as follows:
-- Assignee: Kerry's Bromeliad Nursery, Inc., Apopka, FL (US) --

Signed and Sealed this

Thirty-first Day of March, 2009

JOHN DOLL
*Acting Director of the United States Patent and Trademark Office*